United States Patent
Antonopoulos et al.

(10) Patent No.: US 11,910,839 B2
(45) Date of Patent: Feb. 27, 2024

(54) CASE FOR AEROSOL-GENERATING DEVICE WITH DETECTOR

(71) Applicant: Philip Morris Products S.A., Neuchatel (CH)

(72) Inventors: Roland Antonopoulos, Neuchatel (CH); Kok Hwa Liew, Singapore (SG); Franck Pourrat, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 490 days.

(21) Appl. No.: 17/286,726

(22) PCT Filed: Oct. 21, 2019

(86) PCT No.: PCT/EP2019/078608
§ 371 (c)(1),
(2) Date: Apr. 19, 2021

(87) PCT Pub. No.: WO2020/083850
PCT Pub. Date: Apr. 30, 2020

(65) Prior Publication Data
US 2021/0386124 A1    Dec. 16, 2021

(30) Foreign Application Priority Data
Oct. 22, 2018   (EP) .................................... 18201847

(51) Int. Cl.
*A24F 40/53*   (2020.01)
*A24F 40/95*   (2020.01)
(Continued)

(52) U.S. Cl.
CPC .............. *A24F 40/53* (2020.01); *A24F 40/51* (2020.01); *A24F 40/60* (2020.01); *A24F 40/95* (2020.01)

(58) Field of Classification Search
CPC .......... A24F 40/53; A24F 40/95; A24F 40/51; A24F 40/60; A24F 15/01; A24F 15/12
See application file for complete search history.

(56) References Cited

U.S. PATENT DOCUMENTS 5,692,492 A   12/1997   Bruna et al.
7,116,228 B1  10/2006   Singleton
(Continued)

FOREIGN PATENT DOCUMENTS

CN   201813848 U   5/2011
CN   106170215 A   11/2016
(Continued)

OTHER PUBLICATIONS

International Search Report and Written Opinion dated Jan. 22, 2020 in PCT/EP2019/078608 filed on Oct. 21, 2019.
(Continued)

*Primary Examiner* — Tho D Ta
(74) *Attorney, Agent, or Firm* — Oblon, McClelland, Maier & Neustadt, L.L.P.

(57) ABSTRACT

A case for an aerosol-generating device is provided, the case including a housing; a holder to receive a portion of the device, the holder being movably couplable to the housing and movable relative to the housing between an open position configured to receive the device and a closed position configured to store the device; a holder position detector configured to detect whether the holder is in the open position or the closed position, the holder position detector including circuitry configured to determine a position of the holder relative to the housing; a power supply; an electrical connector configured to electrically connect the power supply to an aerosol-generating device received in the holder; and power supply control circuitry configured to control a supply of power from the power supply to the (Continued)

device received in the holder and connected to the electrical connector.

14 Claims, 5 Drawing Sheets

(51) Int. Cl.
*A24F 40/51* (2020.01)
*A24F 40/60* (2020.01)

(56) References Cited

U.S. PATENT DOCUMENTS

| | | | |
|---|---|---|---|
| 9,247,773 B2* | 2/2016 | Memari | A24F 40/60 |
| 2014/0014125 A1 | 1/2014 | Fernando et al. | |
| 2015/0245654 A1 | 9/2015 | Memari et al. | |
| 2015/0245655 A1 | 9/2015 | Memari et al. | |
| 2015/0245656 A1 | 9/2015 | Memari et al. | |
| 2015/0245657 A1 | 9/2015 | Memari et al. | |
| 2015/0245662 A1 | 9/2015 | Memari et al. | |
| 2015/0245663 A1 | 9/2015 | Memari et al. | |
| 2015/0245664 A1 | 9/2015 | Memari et al. | |
| 2015/0245665 A1 | 9/2015 | Memari et al. | |
| 2015/0245666 A1 | 9/2015 | Memari et al. | |
| 2015/0245667 A1 | 9/2015 | Memari et al. | |
| 2015/0245668 A1 | 9/2015 | Memari et al. | |
| 2015/0359266 A1 | 12/2015 | Memari et al. | |
| 2016/0050975 A1* | 2/2016 | Worm | A24F 40/95 131/328 |
| 2016/0150824 A1 | 6/2016 | Memari et al. | |
| 2016/0192712 A1 | 7/2016 | Memari et al. | |
| 2016/0192713 A1 | 7/2016 | Memari et al. | |
| 2016/0245666 A1 | 8/2016 | McQuillan et al. | |
| 2016/0280450 A1 | 9/2016 | Hearn et al. | |
| 2017/0150758 A1 | 6/2017 | Fernando et al. | |
| 2017/0222468 A1* | 8/2017 | Schennum | H01M 10/46 |
| 2017/0360105 A1 | 12/2017 | Memari et al. | |
| 2017/0360106 A1 | 12/2017 | Memari et al. | |
| 2017/0360107 A1 | 12/2017 | Memari et al. | |
| 2017/0360108 A1 | 12/2017 | Memari et al. | |
| 2017/0360109 A1 | 12/2017 | Memari et al. | |
| 2017/0360110 A1 | 12/2017 | Memari et al. | |
| 2017/0360111 A1 | 12/2017 | Memari et al. | |
| 2017/0360112 A1 | 12/2017 | Memari et al. | |
| 2017/0360113 A1 | 12/2017 | Memari et al. | |
| 2017/0360114 A1 | 12/2017 | Memari et al. | |
| 2017/0360115 A1 | 12/2017 | Memari et al. | |
| 2017/0360116 A1 | 12/2017 | Memari et al. | |
| 2018/0000162 A1 | 1/2018 | Memari et al. | |
| 2018/0000163 A1 | 1/2018 | Memari et al. | |
| 2018/0020735 A1* | 1/2018 | Bilat | H05B 3/44 131/328 |
| 2018/0049474 A1 | 2/2018 | Memari et al. | |
| 2018/0049475 A1 | 2/2018 | Memari et al. | |
| 2018/0184722 A1 | 7/2018 | Murison et al. | |
| 2018/0271158 A1 | 9/2018 | Memari et al. | |
| 2018/0271159 A1 | 9/2018 | Memari et al. | |
| 2018/0271160 A1 | 9/2018 | Memari et al. | |
| 2018/0271161 A1 | 9/2018 | Memari et al. | |
| 2018/0271162 A1 | 9/2018 | Memari et al. | |
| 2018/0271163 A1 | 9/2018 | Memari et al. | |
| 2018/0271164 A1 | 9/2018 | Memari et al. | |
| 2018/0271165 A1 | 9/2018 | Memari et al. | |
| 2018/0271166 A1 | 9/2018 | Memari et al. | |
| 2018/0271167 A1 | 9/2018 | Memari et al. | |
| 2019/0069603 A1 | 3/2019 | Memari et al. | |

FOREIGN PATENT DOCUMENTS

| | | | |
|---|---|---|---|
| CN | 106572708 A | | 4/2017 |
| EP | 2 454 956 A1 | | 5/2012 |
| GB | 2 512 326 A | | 10/2014 |
| GB | 2542010 A | | 3/2017 |
| JP | 9-117274 A | | 5/1997 |
| JP | 2017-513513 A | | 6/2017 |
| JP | 2018-501789 A | | 1/2018 |
| JP | 2020-521 455 A | | 7/2020 |
| KR | 20180044978 A | * | 5/2018 |
| RU | 2 656 616 C1 | | 6/2018 |
| WO | WO 2013/098411 A1 | | 7/2013 |
| WO | WO 2018/135887 A1 | | 7/2018 |
| WO | WO 2018/202732 A1 | | 11/2018 |
| WO | WO 2018/217030 A1 | | 11/2018 |

OTHER PUBLICATIONS

Combined Russian Office Action and Search Report dated Feb. 3, 2023 in Russian Patent Application No. 2021114197 (with English translation), 19 pages.

Extended European Search Report dated Jun. 24, 2019 in European Patent Application No. 18201847.3, 14 pages.

Japanese Notice of Reasons for Rejection dated Nov. 13, 2023 issued in Japanese Patent Application No. 2021-520608 filed on Oct. 21, 2019, with English Translation, total 12 pages.

Office Action and Search report dated Nov. 6, 2023, in Chinese Patent Application No. 201980064352.4, with English-language Translation, citing documents Nos. 1, 2, 15, and 16.

* cited by examiner

CASE FOR AEROSOL-GENERATING DEVICE WITH DETECTOR

The present invention relates to aerosol-generating systems and particularly to electrically operated aerosol-generating systems having an aerosol-generating device and a case for receiving the aerosol-generating device.

Known electrically operated aerosol-generating systems generally comprise an aerosol-generating device having an atomiser and an electrical power supply for supplying power to the atomiser. The atomiser may be an electric heater. Known systems also generally comprise an aerosol-forming substrate which is received by the device and atomised by the atomiser to release volatile compounds in the aerosol-forming substrate which form an aerosol for inhalation by a user. Some known systems also comprise a case for receiving the aerosol-generating device when not in use. Cases in different systems are known to provide different functions, such as protecting the device when not in use, recharging the battery of the device and in some instances, where the aerosol-forming substrate is a liquid aerosol-forming substrate, refilling the device with liquid aerosol-forming substrate.

In some known aerosol-generating systems, the aerosol-generating device is configured to receive an aerosol-generating article comprising a solid aerosol-forming substrate, such as a gathered, crimped sheet of tobacco. In these systems, the device typically comprises an atomiser in the form of a heater blade, which is arranged to penetrate the solid aerosol-forming substrate when the article is received in the device and heat the aerosol-forming substrate from the inside. When the article is removed from the device, a small amount of residue from the aerosol-forming substrate may remain on the heater blade. It is known to clean the residue from the heater blade by pyrolysis, wherein the device is configured to heat the heater blade to a high temperature, higher than the operating temperature at which the heater blade heats the aerosol-forming substrate, to remove residue from the heater blade by thermal degradation. In systems comprising a case, it may be preferable to perform a pyrolysis cycle when the device is received in the case. It is generally advantageous to perform a pyrolysis cycle when an aerosol-generating device is in a case, as the case may provide additional protection to a user from the heater blade as it is heated to the high temperature required for thermal decomposition of the residue.

It would be desirable to provide a case for an aerosol-generating device which collects information about the device. It would be particularly desirable to provide a case for an aerosol-generating device which tracks usage of the device. It would also be desirable to provide a case that enhances the user experience of the device and the aerosol-generating system.

According to a first aspect of the present invention, there is provided a case for an aerosol-generating device, the case comprising: a housing; a holder for receiving a portion of an aerosol-generating device, the holder being movably couplable to the housing and movable relative to the housing between an open position for receiving an aerosol-generating device and a closed position for storing an aerosol-generating device; and a holder position detector adapted to detect whether the holder is in the open position or the closed position.

Providing a case with a holder position detector enables the case to determine the position of the holder relative to the housing. Advantageously, this may enable the case to track usage of the aerosol-generating device. For example, movement of the holder from the closed position to the open position may indicate that a user has opened the case to remove the device from the holder and movement of the holder from the open position to the closed position may indicate that the user has finished a user experience and has replaced the device in the case for storage between uses. As a result, monitoring the position of the device holder may provide an indication of the number of times the device is removed from the case for use.

As used herein, the term 'open position' is used to describe positions or orientations of the holder relative to the housing in which the aerosol-generating device may be received by the holder and removed from the holder. Similarly, as used herein the term 'closed position' is used to describe positions of the holder relative to the housing in which the aerosol-generating device may be substantially prevented or inhibited from being received by the holder and in which the aerosol-generating device may be substantially prevented or inhibited from being removed from the holder.

As used herein, the term 'aerosol-generating device' refers to a device that interacts with an aerosol-forming substrate to generate an aerosol. In certain embodiments, an aerosol-generating device may heat an aerosol-forming substrate to facilitate the release of the volatile compounds from the aerosol-forming substrate. An aerosol-generating device may interact with an aerosol-generating article comprising an aerosol-forming substrate or a cartridge comprising an aerosol-forming substrate. An electrically operated aerosol-generating device may comprise an atomiser, such as an electric heater, to heat the aerosol-forming substrate to form an aerosol.

As used herein, the term 'aerosol-generating article' refers to an article comprising an aerosol-forming substrate capable of releasing volatile compounds which can form an aerosol. In certain embodiments, the aerosol-generating article may comprise an aerosol-forming substrate capable of releasing volatile compounds upon heating, which can condense to form an aerosol.

The holder position detector may be any type of detector suitable for detecting or sensing the position of the holder relative to the housing.

It is envisaged that in some embodiments the holder position detector may comprise a sensor adapted to sense the position of the holder relative to the housing. The sensor may be any suitable type of sensor.

The sensor may be a proximity sensor. As used herein, a proximity sensor is a sensor adapted to detect the presence of objects near or in the vicinity of the sensor. The proximity sensor may be any suitable type of proximity sensor. For example, the proximity sensor may be capacitive, inductive, magnetic or ultrasonic. In particular, the sensor may be an optical proximity sensor. An optical proximity sensor may comprise a light source and an optical transducer arranged to receive reflected light from the light source when an object is arranged near or in the vicinity of the sensor. Preferably, the proximity sensor is an infra-red proximity sensor. An infra-red proximity sensor may utilise a light source which emits light in the infra-red range of the electromagnetic spectrum, typically having wavelengths within the range of about 700 nanometres to about 1100 nanometres.

The sensor may be arranged at any suitable location on or in the case to detect relative positions of the holder and the housing. In some embodiments, the sensor may be arranged on or in the holder and may be configured to sense the position of the housing or one or more of the components housed within the housing relative to the holder. In some preferred embodiments, the sensor may be arranged on or in the housing and configured to sense the position of the holder relative to the housing. In some particularly preferred embodiments, the sensor may be arranged to sense the presence of the device within the holder. For example, the sensor may be arranged to detect the device when the device is received in the holder and the holder is in the closed position. The sensor may be arranged such that the sensor does not detect the holder alone when the holder is in the closed position and the aerosol-generating device is not received in the holder.

In some preferred embodiments, the holder position detector may comprise a switch. In particular, the holder position detector may comprise a mechanical switch having a button or a lever that is movable to open or close an electric circuit. The switch may be actuable between an open position and a closed position. The switch may be biased to one of the open or closed positions. In other words, the switch may be urged to return to one of the open or closed positions in the absence of an external force in the opposite direction. In some embodiments, the switch may be a push-button switch. As used herein, a push-button switch refers to a switch comprising a button that is movable linearly along an axis between an open position and a closed position. In some embodiments, the switch may be a toggle switch or lever switch. As used herein, a toggle switch or lever switch refers to a switch comprising a lever that is movable, generally rotatable, between an open position and a closed position.

In some preferred embodiments, the holder position detector comprises a switch arranged to be actuated on movement of the holder relative to the case between the open position and the closed position.

In some embodiments, the switch is arranged on or within the holder. In these embodiments, the housing or one or more of the components housed within the housing may comprise a switch engaging portion configured to actuate the switch when the holder is moved between the open position and the closed position. In some of these embodiments, the switch engaging portion may comprise a protrusion from the housing or a shaping of the housing that contacts and actuates the switch on movement of the holder relative to the housing.

In some preferred embodiments, the switch is arranged on or within the housing. In these embodiments, the holder may comprise a switch engaging portion adapted to actuate the switch when the holder is moved between the open position and the closed position. In some of these embodiments, the switch engaging portion may comprise a protrusion from the holder or a shaping of the holder that contacts and actuates the switch on movement of the holder relative to the housing.

In some preferred embodiments, the holder position detector comprises circuitry adapted to determine the position of the holder relative to the housing.

In embodiments in which the holder position detector comprises a sensor, the sensor may be connected to the circuitry and the circuitry may be configured to receive signals from the sensor. The signals include information about the position of the holder relative to the housing.

In embodiments in which the holder position detector comprises a switch, the switch may be connected to the circuitry and the circuitry may be configured to monitor the status of the switch. The status of the switch (for example, open or closed) may indicate the position of the holder relative to the housing.

The circuitry may include an integrated circuit, such as a microprocessor.

In some preferred embodiments, the holder position detector circuitry is adapted to count each movement of the holder from at least one of the closed position to the open position and the open position to the closed position. In some embodiments, the holder position detector circuitry is adapted to count each movement of the holder from the closed position to the open position. In some embodiments, the holder position detector circuitry is adapted to count each movement of the holder from the open position to the closed position. Advantageously, counting movements of the holder relative to the housing may enable the case to track usage of the aerosol-generating device.

In some embodiments, the holder position detector circuitry is adapted to compare the count of each movement of the holder to a threshold value. The holder position detector circuitry may be adapted to compare the count of the number of movements of the holder from the closed position to the open position to a threshold value. The holder position detector circuitry may be adapted to compare the count of the number of movements of the holder from the open position to the closed position to a threshold value.

In some embodiments, the holder position detector comprises an aerosol-generating device detector. The aerosol-generating device detector is configured to detect the presence of an aerosol-generating device in the holder. In embodiments wherein the holder position detector comprises a sensor, the sensor may also be configured as the aerosol-generating device detector. In some embodiments, the case comprises an electrical connector for electrically connecting to an aerosol-generating device received in the holder. In these embodiments, the aerosol-generating device detector may comprise the electrical connector and circuitry connected to the electrical connector.

In embodiments wherein the holder position detector comprises an aerosol-generating device detector, the holder position detector circuitry may be configured to count the number of times that the aerosol-generating device is received in the holder. In preferred embodiments, the holder position detector circuitry is configured to count the number of times the holder is in the closed position and the aerosol-generating device is received in the holder. Advantageously, this may enable more accurate monitoring of usage of the aerosol-generating device than counting the number of times the holder is moved between the open and closed positions alone.

In some preferred embodiments, the case comprises means for recharging the power supply of an aerosol-generating device received in the holder. In these preferred embodiments, the case may be referred to as a charging case.

In these preferred embodiments, the case comprises a power supply. The power supply may be any suitable types of electrical power supply. For example, the power supply may comprise one or more batteries and capacitors. The power supply may comprise a lithium ion battery. Preferably, the power supply is a rechargeable electrical power supply.

The case may further comprise an electrical connector. The electrical connector may be configured to electrically connect the power supply of the case to an aerosol-generating device received in the holder. The electrical connector may be any suitable type of electrical connector for electrically connecting to an aerosol-generating device received in the holder. The electrical connector may comprise any suitable number of electrical contacts. Preferably, the electrical connector comprises a plurality of electrical contacts. The electrical connector may be configured to transfer power from the power supply of the case to an aerosol-generating device received in the case. The electrical connector may be configured to transfer data from the case to the aerosol-generating device. In some embodiments, the transfer of data may be one-way, such as from the case to the aerosol-generating device. In other embodiments, the transfer of data may be two-way, from the aerosol-generating device to the case and from the case to the aerosol-generating device. The electrical connector may have at least one electrical contact arranged to transfer electrical power. The electrical connector may have at least one electrical contact arranged to transfer an electrical signal comprising data.

The case may further comprise power supply control circuitry. The power supply control circuitry may be configured to control the supply of power from the power supply of the case to the electrical connector. The power supply control circuitry may be configured to control the supply of power from the power supply of the case to an aerosol-generating device received in the holder and connected to the electrical connector. The power supply control circuitry may be any suitable electrical circuitry. In some embodiments, the power supply control circuitry may be integral with the holder position detector circuitry. In some embodiments, the power supply control circuitry may be separate from the holder position detector circuitry.

The power supply control circuitry is configured to supply power from the power supply of the case to the electrical connector for recharging the power supply of an aerosol-generating device received in the holder. The power supply control circuitry may be configured to supply power from the power supply to the electrical connector when the holder position detector indicates that the detector is in the closed position. The power supply control circuitry may be configured to prevent the supply of power from the power supply to the electrical connector when the holder position detector indicates that the holder is in the open position.

In embodiments wherein the holder position detector comprises an aerosol-generating device detector, the power supply control circuitry may be configured to supply power from the power supply to the electrical connector for recharging an aerosol-generating device when the aerosol-generating device detector indicates that an aerosol-generating device is received in the holder. The power supply control circuitry may be configured to supply power from the power supply to the electrical connector when the aerosol-generating device detector indicates that an aerosol-generating device is received in the holder and the holder is in the closed position. The power supply control circuitry may be configured to prevent the supply of power from the power supply to the electrical connector when the aerosol-generating device detector indicates that an aerosol-generating device is not received in the holder.

In some embodiments, the power supply control circuitry may be configured to monitor the charge level of the power supply of an aerosol-generating device received in the holder. The power supply control circuit may be configured to monitor the charge level of the power supply of an aerosol-generating device by monitoring one or more of the voltage and the current supplied to the aerosol-generating device from the power supply of the case.

The power supply control circuitry may be configured to initiate a charging cycle when it is determined that an aerosol-generating device is received in the holder and the holder is in the closed position. A charging cycle may comprise supplying power from the power supply of the case to the power supply of the aerosol-generating device until the power supply of the aerosol-generating device is fully charged. When the power supply control circuitry determines that the power supply of the aerosol-generating device is fully charged, the power supply control circuitry may end the charging cycle by preventing the supply of power from the power supply of the case to the power supply of the aerosol-generating article.

The case may further comprise an electrical connector for connecting the power supply of the case to an external power supply for recharging the power supply of the case. The case may comprise any suitable electrical connector for connecting the power supply of the case to an external power supply.

In some embodiments, the holder position detector circuitry is configured to supply a signal to an aerosol-generating device received in the holder. In some embodiments, the holder position detector circuitry is configured to supply a signal to an aerosol-generating device received in the holder and connected to the electrical connector when the holder position detector circuitry determines that the holder is in the closed position and the count of each movement of the holder exceeds a threshold value. The signal may be any suitable type of signal. The signal may comprises information or data. The signal may comprises information or data relating to usage of the device. The signal may comprise an instruction for operating the aerosol-generating device.

Preferably, the signal is sent over a wired connection between the case and the aerosol-generating device. Particularly preferably, the signal is sent via the electrical connectors of the case and device when the electrical connectors are electrically connected. However, it is envisaged that in some embodiments the signal may be sent over a wireless connection between the case and the aerosol-generating device. In these embodiments, the case comprises a transmitter for sending the signal to the aerosol-generating device and the aerosol-generating device comprises a receiver for receiving the signal.

In some preferred embodiments, the case is configured to receive an aerosol-generating device comprising: a heater arranged to heat an aerosol-forming substrate; a power supply and control circuitry configured to control the supply of power from the power supply to the heater. In these preferred embodiments, the control circuitry of the aerosol-generating device may be configured to perform a cleaning cycle when the aerosol-generating device is received in the case. The cleaning cycle may comprise supplying power to the heater, typically a higher power than in normal operation, to raise the temperature of the heater to a temperature sufficient to thermally degrade aerosol-forming substrate residue on the heater. Such a cleaning cycle may also be referred to as a pyrolysis cycle. The heater may be heated to any suitable temperature during a cleaning cycle to thermally degrade aerosol-forming substrate residue on the heater. For example, the heater may be heated to a temperature of between about 400 degrees Celsius and about 700 degrees Celsius. In some preferred embodiments, organic materials deposited on the heating element may be thermally liberated by raising the temperature of the heater to about 430 degrees Celsius or greater. For example, the temperature may be raised to 475 degrees Celsius or greater, or 550 degrees Celsius or greater. The temperature of the heater may be raised to higher temperatures, such as 600 degrees Celsius or greater, or 800 degrees Celsius or greater.

A cleaning cycle may be performed for any suitable length of time. It is preferable that the heater is held at a high temperature for a period of time to effect thermal liberation of organic compounds. Typically, a cleaning cycle is performed over a predetermined period of time. For example, the predetermined period of time may be between about 10 seconds and about 7 minutes, between about 30 seconds and about 5 minutes, or between about 2 minutes and about 4 minutes. In some preferred embodiments, the heater may be held at a high temperature in a cleaning cycle for at least 5 seconds. Preferably, the heater is held at a high temperature in a cleaning cycle for a period of between about 5 seconds and about 60 seconds, for example between about 10 seconds and about 30 seconds Preferably, the aerosol-generating device comprises an electrical connector. The electrical connector may be complementary to the electrical connector of the case. The electrical connector of the aerosol-generating device may be arranged to electrically connect to the electrical connector of the case when the aerosol-generating device is received in the holder. The electrical connector of the aerosol-generating device may be arranged to electrically connect to the electrical connector of the case when the aerosol-generating device is received in the holder and the holder is in the closed position. The power supply control circuitry of the case may be configured to supply power to the power supply of the aerosol-generating device when the electrical connectors are electrically connected. The holder position detector circuitry of the case may be configured to send a signal to the control circuitry of the aerosol-generating device when the electrical connectors are electrically connected.

In some preferred embodiments, the holder position detector circuitry of the case may be configured to send a signal to the aerosol-generating device to initiate a cleaning cycle. Such a signal is also referred to herein as a "cleaning signal". The holder position detector circuitry of the case may be configured to send a cleaning signal to an aerosol-generating device to initiate a cleaning cycle when the holder position detector indicates that an aerosol-generating device is received in the holder and the holder is in the closed position. In these embodiments, the control circuitry of the aerosol-generating device is configured to perform the cleaning cycle on receiving the signal from the power supply control circuitry of the case. Advantageously, this may inhibit or prevent the aerosol-generating device from performing the cleaning cycle when the aerosol-generating device is outside of the case. Performing the cleaning cycle only when the aerosol-generating device is received in the case may help to further protect a user from coming into contact with the heater of the device when the heater is heated to the high temperature required for the cleaning cycle.

In some embodiments, the control circuitry of the aerosol-generating device is configured to supply power from the power supply of the aerosol-generating device to the heater during a cleaning cycle. However, in some embodiments the control circuitry of the aerosol-generating device is configured to supply power from the electrical connector of the aerosol-generating device to the heater during a cleaning cycle. This may enable power to be supplied from the power supply of the case directly to the heater of the aerosol-generating device during the cleaning cycle. This may enable a higher power to be supplied to the heater than possible from the power supply of the aerosol-generating device.

In particularly preferred embodiments, the holder position detector circuitry is configured to increment a counter each time it is determined that an aerosol-generating device is received in the holder and the holder is in the closed position. The holder position detector circuitry is further configured to compare the counter to one or more threshold values and to send a cleaning signal to the aerosol-generating device if the counter is equal to or greater than one or more of the threshold values. The one or more threshold values may be predetermined values that are stored in a memory of the holder position detector circuitry. The one or more threshold values may be predetermined values that indicate the maximum number of times which the aerosol-generating device should be used between cleaning cycles. A first threshold value may indicate a first ideal number of times that a device is used between cleaning cycles. The first threshold value may be any suitable value, such as between 3 and 30, between 5 and 25, between 7 and 20 or one of 10, 11, 12, 13, 14 or 15. A second threshold value, larger than the first threshold value, may indicate the maximum number of times that a device should be used between cleaning cycles. The second threshold value may be any suitable value, such as between 5 and 40, between 10 and 35, between 15 and 30 or one of 20, 21, 22, 23, 24 and 25.

The holder position detector circuitry may be configured to reset the counter to zero when a cleaning signal is sent to the aerosol-generating device. Resetting the counter to zero when a cleaning signal is sent to the aerosol-generating device may indicate that the aerosol-generating device has just undergone a cleaning cycle.

In some embodiments, the holder position detector circuitry is configured to send a disabling signal to the aerosol-generating device when it is determined that the counter is equal or greater than one or more of the threshold values. When the control circuitry of the aerosol-generating device receives the disabling signal, the control circuitry is configured to prevent power from being supplied to the heater until a cleaning signal is received. This may ensure that the aerosol-generating device is not used again before a cleaning cycle has been performed. The holder position detector circuitry may be configured to send the disabling signal at any suitable time. Typically, the holder position detector circuitry is configured to send the disabling signal before a charging cycle is initiated.

The holder position detector circuitry may be configured to send a cleaning signal to the aerosol-generating device at any suitable time. For example, the holder position detector circuitry may be configured to send a cleaning signal to the aerosol-generating device after a charging cycle of the aerosol-generating device has been completed. This may ensure that the power supply of the aerosol-generating device has sufficient charge to conduct a cleaning cycle. This may also prioritise charging of the power supply of the aerosol-generating device over cleaning of the aerosol-generating device, such that the device may be sufficiently charged for use before being cleaned. By prioritising charging of the power supply of the aerosol-generating device over cleaning, a user may remove the device from the case, if desired, before the cleaning cycle is initiated.

The holder position detector circuitry is preferably configured to prevent a cleaning signal from being sent to the aerosol-generating device when it is determined that the holder is in the open position. This may help to further protect a user from coming into contact with the heater of the device when the heater is heated to the high temperature required for the cleaning cycle.

In some embodiments, the holder position detector circuitry may also be configured to prevent a cleaning signal from being sent to the aerosol-generating device until an external power supply is connected to the power supply of the case. This may ensure that the power supply of the case has sufficient charge to supply power to the aerosol-generating device throughout the cleaning cycle. In some embodiments, the power supply control circuitry of the case may also be configured to supply power directly from the external power supply to the aerosol-generating device via the electrical connector.

In particularly preferred embodiments, the holder position detector circuitry is configured to trigger a cleaning cycle in the aerosol-generating device when it is determined that the aerosol-generating device is in the holder, the holder is in the closed position, the counter is equal to or greater than the first threshold value, but less than the second threshold value. In some embodiments, the holder position detector circuitry requires a further condition for triggering a cleaning cycle by requiring that the case is connected to an external power supply. Preferably, the holder position detector circuitry is configured to send a cleaning signal to the aerosol-generating device after a charging cycle has completed.

In the particularly preferred embodiments, the holder position detector circuitry is further configured to send a disabling signal to the aerosol-generating device when it is determined that the counter is greater than or equal to the second threshold value. When the control circuitry of the aerosol-generating device receives the disabling signal, the control circuitry is configured to prevent power from being supplied to the heater until a cleaning signal is received. The holder position detector circuitry is configured to send the disabling signal before a charging cycle is initiated. After the charging cycle is completed, the control circuitry is configured to send a cleaning signal to the aerosol-generating device. This should help to ensure that an aerosol-generating device is not used an excessive amount of times between cleaning cycles, such that residue on the heater impacts on aerosol generation and composition. When it is determined that the counter is equal to or greater than the second threshold value, the number of conditions for sending a cleaning signal may be reduced. For example, it may not be required that the case is connected to an external power supply before a cleaning signal is sent. The holder position detector circuitry may merely require that the charge level of the power supply of the case is above a minimum level, an aerosol-generating device is received in the holder and the holder is in the closed position.

The case may have any suitable size and shape for receiving an aerosol-generating device. Typically, the case is portable. In other words, the case has a suitable size and shape to be carried by a user. Preferably, the case is a handheld case. In other words, the case has a suitable size to be held in a hand of a user. The case may have a size and shape similar to a conventional packet of cigarettes. The case may have any suitable diameter and any suitable length. The case may have a length between about 50 mm and about 200 mm. The case may have an external diameter between about 10 mm and about 50 mm.

The case may have a transverse cross-section of any suitable shape. For example, the case may have a substantially circular, elliptical, triangular, square, rhomboidal, trapezoidal, pentagonal, hexagonal or octagonal transverse cross-section. In some particular embodiments, the aerosol-generating device has a substantially rectangular transverse cross-section. The case may have a substantially constant transverse cross-section along its length. The case may have a substantially rectangular transverse cross-section along its length. In particular embodiments, the case may be a substantially rectangular cuboid.

As used herein, the term 'longitudinal' is used to describe the direction between a downstream, proximal or mouth end and the opposed upstream or distal end and the term 'transverse' is used to describe the direction perpendicular to the longitudinal direction.

As used herein, the term 'length' is used to describe the maximum longitudinal dimension between the distal or upstream end and the proximal or downstream end of components, aerosol-generating devices, aerosol-generating articles and cases.

As used herein, the terms 'diameter' and 'width' are used to describe the maximum transverse dimension of components, aerosol-generating devices, aerosol-generating articles and cases.

As used herein, the term 'transverse cross-section' is used to describe the cross-section of components, aerosol-generating devices, aerosol-generating articles and cases in the direction perpendicular to the major axis of the components, aerosol-generating devices, aerosol-generating articles and cases, respectively.

As used herein, the terms 'upstream', 'downstream', 'proximal' and 'distal' are used to describe the relative positions of components, or portions of components, of aerosol-generating devices, aerosol-generating articles and cases.

The housing of the case may generally form the shape of the case. The housing may comprise one or more walls. In particular embodiments, the housing may be a substantially rectangular cuboid.

The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. In particular embodiments, the material is light and non-brittle.

The housing comprises an opening. The opening may be any suitable size and shape. The opening may generally be sized and shaped to receive the holder and the aerosol-generating device when the aerosol-generating device is received in the holder. The opening may generally be sized and shaped to receive the one or more internal walls of the holder and the aerosol-generating device. In some particular embodiments, the opening of the housing may extend substantially over or along one side of the housing. In these embodiments, the case may generally form a rectangular box that is open at one side.

The housing defines a cavity or a space for receiving the holder and an aerosol-generating device received in the holder. The cavity or space is an open cavity or space, such that the holder and the aerosol-generating device may be inserted into the cavity or space through the opening of the housing. The cavity or space may be configured to receive at least one or more internal walls of the holder and an aerosol-generating device received in the holder when the holder is in the closed position. Typically, the cavity or space is configured to receive the entire aerosol-generating device when the holder is in the closed position. Advantageously, this may enable the aerosol-generating device to be entirely enclosed within the cavity or space and may enable the case to protect the aerosol-generating device from the external environment.

The holder is configured to receive the aerosol-generating device. The holder may be a drawer or a cradle that is sized to hold or contain the aerosol-generating device. Preferably, the holder comprises an external wall and one or more internal walls. The external wall and the one or more internal walls are arranged to releasably hold the aerosol-generating device. In some embodiments, the one or more internal walls are attached or joined to the external wall. In other embodiments, the one or more internal walls are integrally formed with the external wall. The holder may be formed from any suitable material. Typically, the holder is formed from the same material as the housing of the case. The external wall may and the one or more internal walls may be formed from the same material. The external wall and the one or more internal walls may be made from different materials.

The holder may be any suitable size and shape for receiving the aerosol-generating device.

The external wall and the one or more internal walls may be configured in any suitable configuration to releasably hold the aerosol-generating device. The external wall and the one or more internal walls may be arranged to define a passage or a channel for receiving the aerosol-generating device. The passage or channel may have any suitable size and shape. Typically, the passage or channel may have a substantially similar size and shape to the aerosol-generating device. The passage or channel may have any suitable transverse cross-section. For example, the passage or channel may have a substantially circular, elliptical, triangular, square, rhomboidal, trapezoidal, pentagonal, hexagonal or octagonal transverse cross-section. Typically, the transverse cross-section of the passage or channel is substantially circular. The passage or channel may have any suitable length. Typically the length of the passage or channel is less than the length of the aerosol-generating device. The transverse cross-section of the passage or channel may be substantially similar along the length of the passage or channel.

The passage or channel may be open at one end. The passage or channel may be open at one end and closed at the other end, opposite the open end. The passage or channel may be open at both ends. Where the passage or channel comprises an open end and a closed end, the open end may be arranged at or around a first end of the holder and the closed end may be arranged at or around a second end of the holder. In some embodiments, the external wall and the one or more internal walls may be arranged to form a tube comprising the passage or the channel.

The external wall of the holder may have any suitable length. The length of the external wall may be substantially equal to the length of the housing of the case. Typically, the length of the external wall of the holder is substantially equal to the length of the aerosol-generating device. In some embodiments, the length of the external wall is greater than the length of the aerosol-generating device. The length of the external wall may be substantially similar to the length of the case. The length of the external wall may be between about 30 mm and about 200 mm.

In some embodiments, the external wall of the holder is configured to cover the opening of the housing when the holder is in the closed position. The opening of the housing has a length and the length of the external wall of the holder may be substantially equal to the length of the opening. In some embodiments, the length of the external wall may be greater than the length of the opening. The opening of the housing has a width and the width of the external wall of the holder may be substantially equal to the width of the opening. In some embodiments, the width of the external wall may be greater than the width of the opening.

The holder may comprise any suitable number of internal walls. The holder may comprise one internal wall. The holder may comprise two or more internal walls. In some embodiments comprising two or more internal walls, the two or more internal walls may be joined or attached together. In some embodiments comprising two or more internal walls, the internal walls may be separate or spaced from each other.

The one or more internal walls may be arranged in any suitable arrangement. In particular, each of the one or more internal walls may be arranged to extend from the external wall. Each of the one or more internal walls may be arranged to extend from the external wall in a direction substantially perpendicular to the external wall. The one or more internal walls may be arranged to substantially extend along the external wall. The one or more internal walls may be arranged to substantially extend along the external wall from at or around the first end of the holder. In some embodiments, the one or more internal walls may be arranged to substantially extend along the external wall from at or around the second end of the holder in a direction towards the first end of the holder. The holder may comprise a portion or region at or around the first end of the holder that does not comprise the one or more internal walls. In some embodiments, holder may also comprise a portion at around the second end of the holder that does not comprise the one or more internal walls.

In some embodiments, the one or more internal walls comprise a pair of opposing internal walls, each of which has one end that is attached to the external wall and an opposite unattached end that is not attached to the external wall or the other opposing internal wall. In these embodiments, an opening or spacing may be provided between the unattached ends of the opposing internal walls. The opening may be smaller or narrower than the diameter of the aerosol-generating device, such that an aerosol-generating device received in the holder, between the pair of opposing internal walls, may not pass through the opening or spacing between the unattached ends of the opposing internal walls.

Where the holder comprises one internal wall, the internal wall may be attached or secured to the external wall at opposite ends to form a tube having a passage for receiving the aerosol-generating device.

Typically, the length of each of the one or more internal walls is less than the length of the external wall. The length of the one or more internal walls of the holder may be between about 10% and about 90% of the length of the external wall, between about 20% and about 80% of the length of the external wall and may be between about 30% and about 70% of the length of the external wall. The length of the one or more internal walls of the holder may be no more than 90% of the length of the external wall, no more than 80% of the length of the external wall, no more than 75% of the length of the external wall or no more than 70% of the length of the external wall. The length of the one or more internal walls may be between about 25 mm and about 190 mm.

The length of the gap between the one or more internal walls and the external wall at the first end of the holder may be between about 5% and about 50% of the length of the external wall, may be between about 10% and about 40% of the length of the external wall and may be between about 10% and about 30% of the length of the external wall. The length of the gap may be between about 5 mm and about 100 mm.

In some embodiments, the opening of the housing may extend substantially over one side of the housing. In some of these embodiments, where the external wall of the holder is configured to cover the opening of the housing when the holder is in the closed position, the external wall of the holder may form a side wall of the housing when the holder is in the closed position. In other words, the housing and the external wall of the holder may form an enclosure when the holder is in the closed position.

The one or more internal walls of the holder may be configured to be received in the housing when the holder is in the closed position, such that when the aerosol-generating device is releasably held in the holder the aerosol-generating device is received in the housing when the holder is in the closed position. The one or more internal walls of the holder may be configured to be received in the cavity of the housing when the holder is in the closed position. Accordingly, an aerosol-generating device received in the holder between the one or more internal walls and the external wall may be received in the cavity of the housing when the holder is in the closed position.

The housing and the external wall of the holder may be arranged to substantially surround or enclose the aerosol-generating device when the aerosol-generating device is received in the holder, and the holder is in the closed position. Accordingly, the case may be configured to provide protection for the aerosol-generating device when the aerosol-generating device is received in the holder and the holder is in the closed position. In these embodiments, the housing and the external wall of the holder may substantially prevent or inhibit access to the aerosol-generating device to a user until the holder is moved from the closed position to the open position. In other words, a user may be substantially prevented from removing the aerosol-generating device from the holder when the holder is in the closed position.

The holder has a first end and a second end, opposite the first end. The holder is movable relative to the housing. In some embodiments, the holder may be slidable relative to the housing. In some preferred embodiments, the holder may be rotatably coupled to the housing. The holder may be rotatably coupled to the housing at around the second end. The rotatable coupling may comprise any suitable type of coupling. For example, the rotatable coupling may comprise one or more of a hinge, a pivot and a linkage.

In some particularly preferred embodiments, the holder comprises a first end having an opening for receiving an aerosol-generating device into the holder and a second end, opposite the first end, the holder being rotatably coupled to the housing at around the second end. The holder may be rotatably couplable to the housing at a position closer to the second end than the first end. In some embodiments, the external wall of the holder may be rotatably couplable to the housing. In some preferred embodiments, the one or more internal walls of the holder may be rotatably couplable to the housing.

The holder may be movable between the open position and the closed position by any suitable means. In some embodiments, the housing may be shaped such that portions of the one or more internal walls are exposed when the holder is in the closed position. The exposed portions of the holder may enable a user to grip or grasp the holder and rotate or pivot the holder from the closed position into the open position. In some embodiments, the housing may comprise one or more scalloped portions for exposing portions of the internal walls of the holder when the holder is in the closed position. In some embodiments, the holder may be movable from the closed position to the open position by pressing on a portion of the holder at or around the first end of the holder. In other words, the holder may be movable from the closed position to the open position by a trigger action.

The case may comprise means for releasably retaining the housing and the holder in the closed position.

In some embodiments, the holder may be configured to have a close fit or a friction fit in the opening of the housing. The close fit or friction fit may releasably retain the housing and the holder in position by friction.

In some embodiments, the case may comprise resilient means, such as a torsion spring. In these embodiments, a user may be required to exert a force against the resilient means to move the holder between the open position and the closed position. In some embodiments, the resilient means may be configured to have more than one stable position, such as a bistable torsion spring. In these embodiments, the bistable spring may be arranged to be in a stable state when the holder is in the open position and when the holder is in the closed position.

In some embodiments, one of the housing and the holder may be provided with a moveable catch for releasably securing the holder in the closed position. In these embodiments, the housing may be provided with a button configured to move the catch when pressed to release the holder from the closed position.

In some embodiments, the holder may be provided with a first magnetic material and the housing may be provided with a second magnetic material. The first and second magnetic materials may be arranged such that the first and second magnetic materials are proximate or adjacent to each other when the holder is in the closed position. The first and second magnetic materials may be arranged such that the first and second magnetic materials are attracted to each other when the holder is in the closed position.

The term 'magnetic material' is used herein to describe a material which is able to interact with a magnetic field, including both paramagnetic and ferromagnetic materials. A magnetisable material may be a paramagnetic material, such that it only remains magnetised in the presence of an external magnetic field. Alternatively, a magnetisable material may be a material which becomes magnetised in the presence of an external magnetic field and which remains magnetised after the external field is removed (a ferromagnetic material, for example). The term "magnetic material" as used herein encompasses both types of magnetisable material, as well as material which is already magnetised.

At least one of the first and second magnetic materials may comprise an alloy of neodymium, such as neodymium, iron and boron. In other words, at least one of the first and second magnetic materials may be a neodymium magnet. At least one of the first and second magnetic materials may comprise a ferromagnetic stainless steel, such as SS430 stainless steel.

Where the case comprises means for releasably retaining the housing and the holder in the closed position, the case may also comprise means for biasing the housing and the holder into the open position. The housing may be provided with one or more springs, arranged to pivot or rotate the holder into the open position.

The case may also comprise retaining means for releasably retaining the aerosol-generating device in the holder.

The retention means may be any suitable means for releasably retaining the aerosol-generating device in the holder. For example, the retention means may comprise a friction fit between the aerosol-generating device and the holder, when the aerosol-generating device is received by the holder. For example, the retention means may comprise resilient means arranged on the housing of the case to urge the aerosol-generating device into the holder when the holder is in the closed position.

In some particular embodiments, the retention means may comprise magnetic retention means. The magnetic retention means may comprise a first magnetic material and a second magnetic material. The first magnetic material may be provided in the aerosol-generating device and the second magnetic material may be provided in the case.

The first and second magnetic materials may be arranged such that the first and second magnetic materials are proximate each other when the aerosol-generating device is received by the holder. The first and second magnetic materials may be arranged such that the first and second magnetic materials are attracted to each other when the aerosol-generating device is received by the holder.

The first magnetic material may be arranged at or towards the distal end of the aerosol-generating device and the second magnetic material may be arranged at or towards the first end of the holder or in the housing towards the first end of the holder when the holder is in the closed position. The first magnetic material may be arranged at a distal end face of the aerosol-generating device. Where the holder comprises a sleeve having a closed end face at or around the first end, the second magnetic material may be arranged at the closed end face of the sleeve. Where the holder comprises an electrical connector part at or around the first end of the holder, the first magnetic material may be arranged at the electrical connector part. Where the holder comprises a sleeve having a closed end face and an electrical connector part at the closed end face, the first magnetic material may be arranged at the electrical connector part.

According to another aspect of the present invention, there is provided an aerosol-generating system comprising an aerosol-generating device and a case for an aerosol-generating device. The aerosol-generating device comprises: a cavity for receiving an aerosol-forming substrate; a heater arranged to heat an aerosol-forming substrate received in the cavity; a power supply; and control circuitry configured to control the supply of power between the power supply and the heater. The case comprises: a housing having an opening; a holder for receiving the aerosol-generating device, the holder being movably couplable to the housing and movable relative to the housing between an open position for receiving the aerosol-generating device and a closed position; and a holder position detector adapted to determine whether the holder is in the open position or the closed position.

In preferred embodiments, the case comprises: a power supply; an electrical connector configured to electrically connect the power supply to an aerosol-generating device received in the holder; and power supply control circuitry configured to control the supply of power from the power supply to an aerosol-generating device received in the holder and connected to the electrical connector. In these embodiments, the holder position detector circuitry of the case may be adapted to count each movement of the holder from at least one of the closed position to the open position and the open position to the closed position and compare the count of each movement of the holder to a threshold value. The holder position detector circuitry of the case may also be configured to supply a signal to the aerosol-generating device when the aerosol-generating device is received in the holder and connected to the electrical connector and when the holder position detector circuitry determines that the holder is in the closed position and the count of each movement of the holder exceeds the threshold value.

In particularly preferred embodiments, the control circuitry of the aerosol-generating device is configured to supply power to the heater in a cleaning cycle when the control circuitry of the aerosol-generating device receives a signal from the holder position detector circuitry of the case.

The aerosol-generating device may have any suitable size and shape.

The aerosol-generating device may be a handheld device. In other words, the aerosol-generating device may have any size and shape suitable to be held in the hand of a user. The aerosol-generating device may have a size and shape similar to a conventional cigarette or cigar. The aerosol-generating device may be portable.

The aerosol-generating device may have a transverse cross-section of any suitable shape. For example, the aerosol-generating device may have a substantially circular, elliptical, triangular, square, rhomboidal, trapezoidal, pentagonal, hexagonal or octagonal transverse cross-section. In some particular embodiments, the aerosol-generating device has a substantially circular transverse cross-section.

The aerosol-generating device may have a substantially constant transverse cross-section along its length. The aerosol-generating device may have a substantially circular transverse cross-section along its length. The device may have rotational symmetry about its longitudinal axis. In particular embodiments, the aerosol-generating device may be substantially circularly cylindrical.

The aerosol-generating device may have any suitable diameter and any suitable length. The aerosol-generating device may be elongate. In some particular embodiments, the aerosol-generating device may have a shape, diameter and length substantially similar to a conventional cigarette or cigar. The aerosol-generating device may have a length between about 30 mm and about 150 mm. The aerosol-generating device may have an external diameter between about 5 mm and about 30 mm.

The aerosol-generating device may be configured to receive one or more of a cartridge, an atomiser and an aerosol-generating article. The aerosol-generating device may be configured to receive one or more of a cartridge, an atomiser and an aerosol-generating article at a proximal end. The device comprises a cavity for receiving an aerosol-forming substrate. The cavity may be adapted to receive one or more of a cartridge, an atomiser and an aerosol-generating article.

In some preferred embodiments, the aerosol-generating device may comprise an atomiser. Where the aerosol-generating device comprises an atomiser, the device may be configured to receive an article comprising an aerosol-forming substrate or a cartridge comprising an aerosol-forming substrate. In other embodiments, the aerosol-generating device may be configured to receive an atomiser or a combination of an atomiser and an article or a cartridge comprising an aerosol-forming substrate. Where the device comprises a cavity for receiving one or more of a cartridge and an aerosol-generating article, the atomizer may be arranged in the cavity.

The aerosol-generating device may comprise a housing. In particular embodiments, the housing may be substantially circularly cylindrical. The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. In particular embodiments, the material is light and non-brittle.

The aerosol-generating device comprises a power supply. The power supply may be any suitable types of electrical power supply. For example, the power supply may comprise one or more batteries and capacitors. The power supply may comprise a lithium ion battery. Preferably, the power supply is a rechargeable electrical power supply.

The aerosol-generating device comprises a proximal end and a distal end, opposite the proximal end. Preferably, the device comprises a cavity for receiving an aerosol-forming substrate at the proximal end. The distal end of the device comprises a distal end face. In preferred embodiments, an electrical connector is arranged at the distal end face. Where the aerosol-generating device is elongate, and substantially extends along a longitudinal axis, the distal end face may be substantially perpendicular to the longitudinal axis.

According to another aspect of the present invention, there is provided a method of initiating a cleaning cycle of an aerosol-generating system, the method comprising:
providing an aerosol-generating device comprising:
a cavity for receiving an aerosol-forming substrate;
a heater arranged to heat an aerosol-forming substrate received in the cavity;
a power supply; and
control circuitry configured to control the supply of power between the power supply and the heater; and
providing a case for receiving the aerosol-generating device, the case comprising:
a housing having an opening;
a holder for receiving the aerosol-generating device, the holder being movably couplable to the housing and movable relative to the housing between an open position for receiving the aerosol-generating device and a closed position; and
a holder position detector adapted to determine whether the holder is in the open position or the closed position;
power supply control circuitry configured to control the supply of power from the power supply to an aerosol-generating device received in the holder and connected to the electrical connector;
counting each movement of the holder from at least one of the closed position to the open position and the open position to the closed position;
comparing the count of each movement of the holder to a threshold value;
supplying a signal to the aerosol-generating device when the aerosol-generating device is received in the holder and connected to the electrical connector and when the holder position detector circuitry determines that the holder is in the closed position and the count of each movement of the holder exceeds the threshold value; and
supplying power to the heater in a cleaning cycle when the aerosol-generating device receives the signal from the case.

It will be appreciated that features described in relation to one aspect of the present invention may also be applied equally to the other aspects of the present invention. Features described in relation to the first aspect of the present invention may be applied equally to the second and third aspects of the present invention and vice versa. Features described in relation to the second aspect of the present invention may be applied equally to the third aspect of the present invention and vice versa.

The invention will be further described, by way of example only, with reference to the accompanying drawings, in which.

Figure 1:
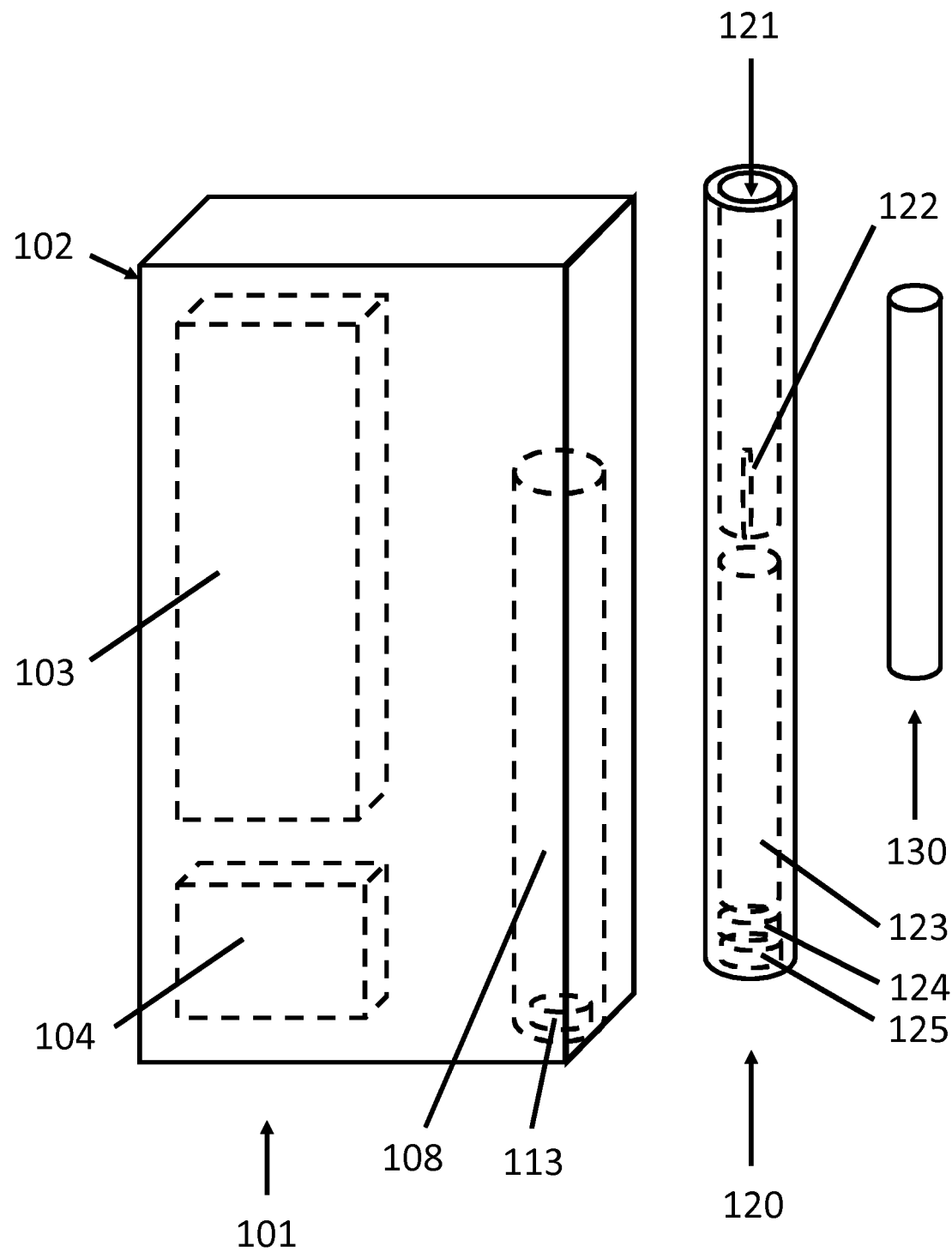
FIG. 1 shows a schematic illustration of a known electrically operated aerosol-generating system comprising an aerosol-generating article, an aerosol-generating device and a case for the electrically operated aerosol-generating article.

FIGS. 1 to 5 show schematic illustrations of a case 101 according to a known electrically operated aerosol-generating system. The known electrically operated aerosol-generating system comprises a case 101, an aerosol-generating device 120 and an aerosol-generating article 130.

The case 101 comprises a housing 102 and a holder 106.

The housing 102 houses a power supply 103, in the form of a lithium ion battery, and electric circuitry 104. The housing 102 also defines a cavity 105 that is shaped and dimensioned to receive a portion of the holder 106 and the aerosol-generating device 120, when the aerosol-generating device 120 is received in the holder 106.

The case 101 is configured to receive the aerosol-generating device 120.

The aerosol-generating device 120 is substantially circularly cylindrical and has the general dimensions of a conventional cigar. The length of the device 120 is substantially identical to the length of the cavity 105 and the diameter of the device 120 is slightly smaller than the diameter of the cavity 105, such that the device 120 fits closely in the cavity 105. The aerosol-generating device 120 comprises an open cavity 121 at a proximal end for receiving the aerosol-generating article 130. The aerosol-generating device 120 further comprises an electric heater 122 arranged in the cavity 121 for heating at least a portion of the aerosol-generating article 130 when the aerosol-generating article 130 is received in the cavity 121. A power supply 123, in the form of a lithium ion battery, is housed in the housing of the device 120 for supplying power to the heater 122 along with control circuitry 124 for controlling the supply of power from the power supply 123 to the heater 122. The aerosol-generating device 120 also comprises an electrical connector part 125 at a distal end face, opposite the proximal end, which is configured to receive power from an external power source for recharging the power supply 123.

The aerosol-generating article 130 comprises an aerosol-forming substrate (not shown) in the form of a gathered, crimped sheet of tobacco, and a filter (not shown) arranged back to back with the aerosol-forming substrate in the form of a rod. The aerosol-generating article 130 has a diameter substantially equal to the diameter of the cavity 121 of the device 120 and a length longer than the cavity 121, such that when the article 130 is received in the cavity 121 of the device 120, the filter extends out of the cavity 121 and may be drawn on by a user, similarly to a convention cigarette.

In use, a user inserts the article 130 into the cavity 121 of the device 120 and turns on the device 120 to activate the electric heater 122. The electric heater 122 heats the aerosol-forming substrate of the article 130 such that volatile compounds of the aerosol-forming substrate are released and condense to form an aerosol. The user may draw on the filter of the article 130 to inhale the aerosol generated from the heated aerosol-forming substrate.

After use, the article 130 may be removed from the device 120 for disposal, and the device 120 may be placed into the case 101 for storage and for charging of the battery of the device 120.

The housing 102 of the case 101 generally forms an open rectangular box having sidewalls defining five sides of the box and an opening at a sixth side of the box. The opening forms an open end of the cavity 105 and extends substantially the length and width of one side of the housing 102.

The holder 106 of the case 101 comprises an external wall 107 and an internal wall 108.

The external wall 107 is elongate and has a length substantially identical to the length of the housing 102. The length of the external wall 107 defines the length of the holder 106. The external wall 107 is shaped and dimensioned to cover the opening of the housing 102. As such, the external wall 107 is shaped and dimensioned as a sixth sidewall of the housing 102.

The internal wall 108 forms a substantially circularly cylindrical tube, defining a generally circularly cylindrical inner passage 109 that extends the length of the internal wall 108. The passage 109 is open at one end and closed at the other end, opposite the open end. The passage 109 has a transverse cross-section along its length that is substantially identical to the transverse-cross section of an aerosol-generating device, the diameter of the inner passage 109 being slightly larger than an aerosol-generating device, such that an aerosol-generating device may be removably held in the inner passage 109 of the holder 106.

The tubular internal wall 108 of the holder 106 is integrally formed with the external wall 107. It will be appreciated that in some embodiments, the internal wall 108 may not be integral with the external wall 107 and may instead be attached to the external wall 108 by any suitable attachment means. The tubular internal wall 108 is arranged with its longitudinal axis substantially aligned with the longitudinal axis of the external wall 108. The closed end of the passage 109 is arranged at a first end of the external wall 107 and the internal wall is arranged to extend along the external wall 107 from the first end towards the second end. The length of the internal wall 108 is less than the length of the external wall 107. As such, the internal wall 108 does not extend along the entire length of the external wall 107. A portion of the holder 106 at the second does not comprise the internal wall 108. In other words, the internal wall 108 does not extend the length of the holder 106 from the first end to the second end. The length of the internal wall 108 is about 70% of the length of the external wall 107. As such, a space or gap 110 is provided between the end of the internal wall 108 towards the second end of the holder 106 and the end of the external wall 107 at the second end of the holder 106.

The holder 106 is pivotally coupled 111 to the housing at the first end. In particular, the external wall 107 is pivotally coupled to the housing 102 at one end of the opening of the cavity 105. The pivotal coupling 111 enables the holder 106 to be pivoted or rotated relative to the housing 102 between an open position, in which the open end of the passage 109 towards the second end of the holder 106 is exposed, and a closed position, in which the open end of the passage 109 is hidden by the housing 102 and the opening of the housing 102 is covered by the external wall 107 of the holder 106.

The internal wall 108 of the holder 106 is received in the cavity 105 of the housing 102 when the holder 106 is rotated into the closed position. When an aerosol-generating device is received in the inner passage 109 of the holder 106, and the holder is rotated into the closed position, the aerosol-generating device is enclosed in the cavity 105, as it is surrounded or enclosed by the walls of the housing 102 and the external wall 107 of the holder 106. In this position, an aerosol-generating device received in the holder may be substantially protected by the case when the holder is in the closed position.

An electrical connector part 113 is arranged at the closed end of the inner passage 109, for engagement with a complimentary electrical connector part at a distal end face of the aerosol-generating device 120 when the aerosol-generating device 120 is received in the inner passage 109. The electrical connector part may be any suitable type of electrical connector part. The electrical connector part is electrically connected to the electric circuitry 104 in the housing 102 of the case 101 via a flexible printed circuit (not shown) that enables movement of the electrical connector part with the holder without damaging the electrical connection.

Figure 2:
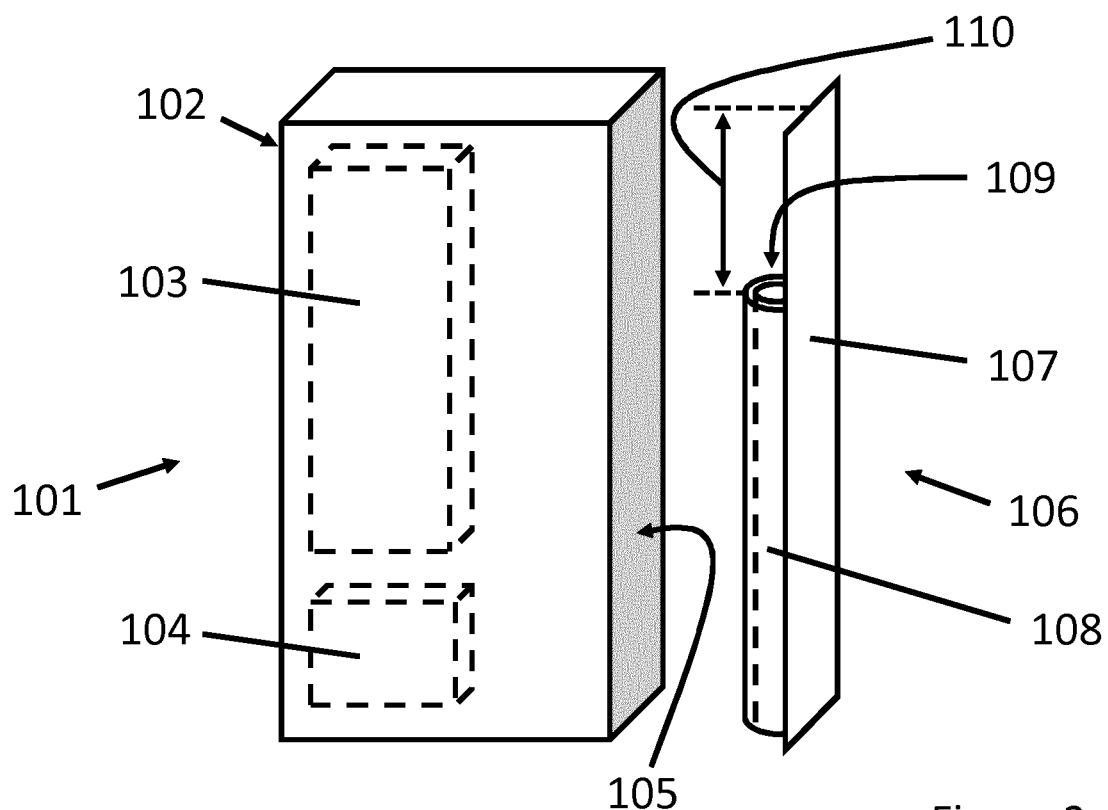
FIG. 2 shows a schematic illustration of the case of FIG. 1 with the holder separated from the housing of the case.
Figure 3:
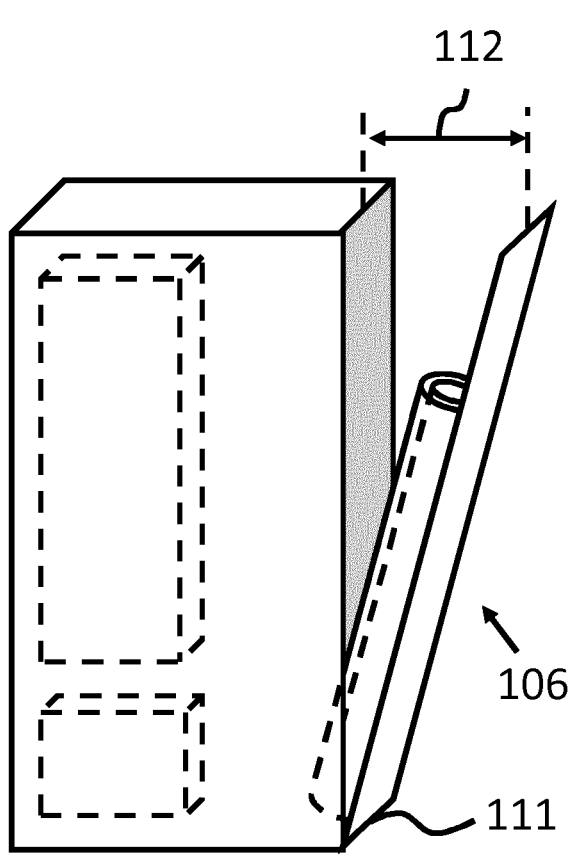
FIG. 3 shows a schematic illustration of the case of FIG. 1 with the holder in an open position.

FIGS. 2 and 3 show schematic illustrations of the case 101 wherein the holder 106 is rotated about the pivotal coupling 111 relative to the housing 102 between the closed position and the open position, respectively.

The holder 106 is pivotable relative to the housing 102 between two predetermined positions, the closed position and the open position. The holder 106 is pivotable in a first direction, to rotate the holder 106 relative to the housing 102 from the open position to the closed position. In this embodiment, the external wall 107 of the holder 106 overlaps with the housing 102 at the second end, such that external wall 107 makes contact with the housing 102 when the holder 106 is in the closed position to prevent the holder 106 from being rotated further in the first direction beyond the closed position. The holder 106 is also pivotable in a second direction, opposite the first direction, to rotate the holder 106 relative to the housing 102 from the closed position to the open position. The cavity 105 of the housing 102 comprises a stop (not shown) which is arranged to contact the internal wall 108 of the holder 106 when the holder 106 is in the open position to prevent the holder 106 from being rotated in the second direction beyond the open position.

FIG. 3 shows the holder 106 in the open position. In this embodiment, in the open position, the opening 112 between the housing 102 and the first end of the external wall 107 of the holder 106 has a width or diameter that is about double the width or diameter of the aerosol-generating device. It will be appreciated that in some embodiments, the holder may be pivotal relative to the housing to different angles, which provide openings between the housing and the first end of the external wall of the holder having different widths.

The wide opening 112 and the gap 110 between the second end of the internal wall 108 and the second end of the external wall 107 enable an aerosol-generating device to be inserted into the holder 106 from a wide range of angles. In particular, the gap 110 enables an aerosol-generating device to make contact with the external wall 107 when the aerosol-generating device is being inserted into the holder 106. This may enable the portion of the external wall 107 without the internal wall 108 at the second end of the holder 106 to be used as a guide for aligning the aerosol-generating device with the passage 109 of the tubular internal wall 108.

This may further facilitate insertion of the aerosol-generating device 20 into the holder 106.

Figure 4:
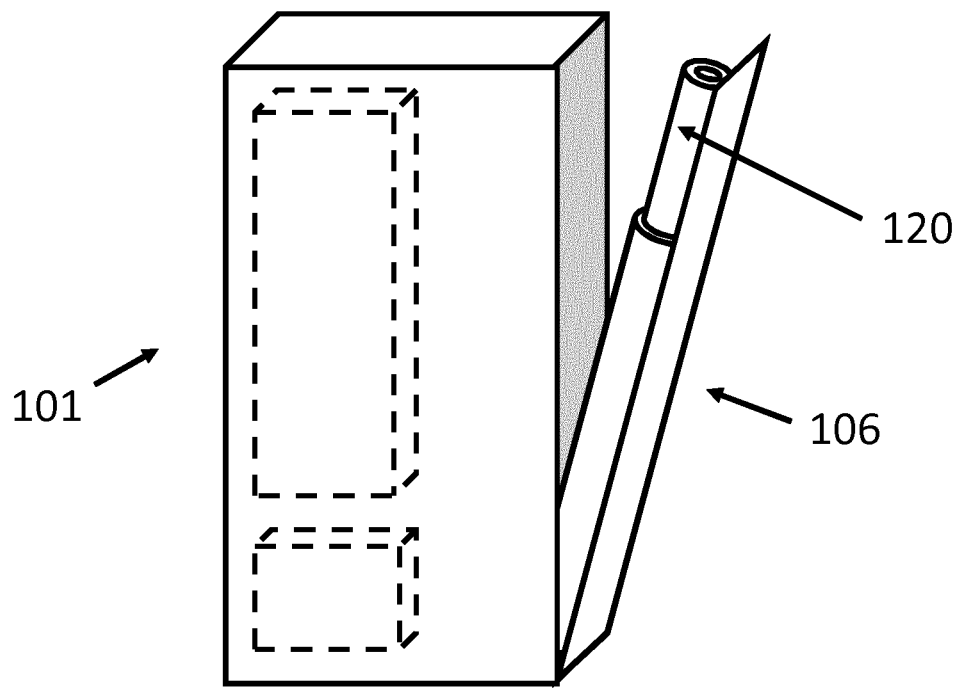
FIG. 4 shows a schematic illustration of the case of FIG. 1 with the holder in an open position and the aerosol-generating device received in the holder.
Figure 5:
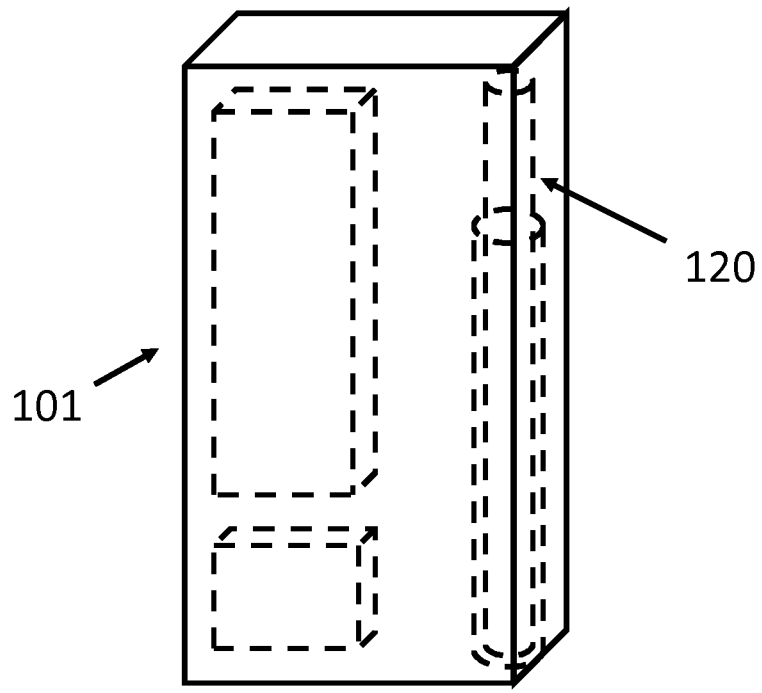
FIG. 5 shows a schematic illustration of the case of FIG. 1 with the aerosol-generating device received in the holder and the holder in a closed position.

FIGS. 4 and 5 show the aerosol-generating device 120 releasably held in the holder 106 with the holder 106 in the closed position and the open position, respectively.

FIG. 4 shows the aerosol-generating device 120 received in the holder 106 with the holder 106 in the open position. As shown in FIG. 4, the gap 110 between the second end of the internal wall 108 and the second end of the external wall 107 exposes a portion of the aerosol-generating device 120 at the proximal end of the device 120. This exposed portion at the proximal end of the device 120 may be accessed and grasped by a user for removing the device 120 from the holder 106. Accordingly, the holder 106 does not require a lifting mechanism for lifting the device 120 out of the holder 106. This may reduce the cost and simplify the design of the holder 106 compared to holders that include lifting mechanisms for removing devices.

FIG. 5 shows the aerosol-generating device 120 held in the holder 106 with the holder 106 in the closed position. The aerosol-generating device 120 is entirely enclosed in the cavity 105 of the housing 102, being surrounded by the housing 102 and the external wall 107 of the holder 106. In this configuration, the aerosol-generating device 120 is substantially protected by the case 101.

An electrical connector 113 is provided at the closed end of the passage 109 for electrically connecting to the electrical connector 125 of the aerosol-generating device 120 to connect the battery 103 of the case 101 to the battery 123 of the device 120 when the generating device 120 is received in the holder 106 and the holder 106 is in the closed position. Accordingly, the case 101 is configured to supply power to the aerosol-generating device 120 for charging the aerosol-generating device 120, when the aerosol-generating device is received in the holder 106 and the holder 106 is in the closed position.

Figure 6:
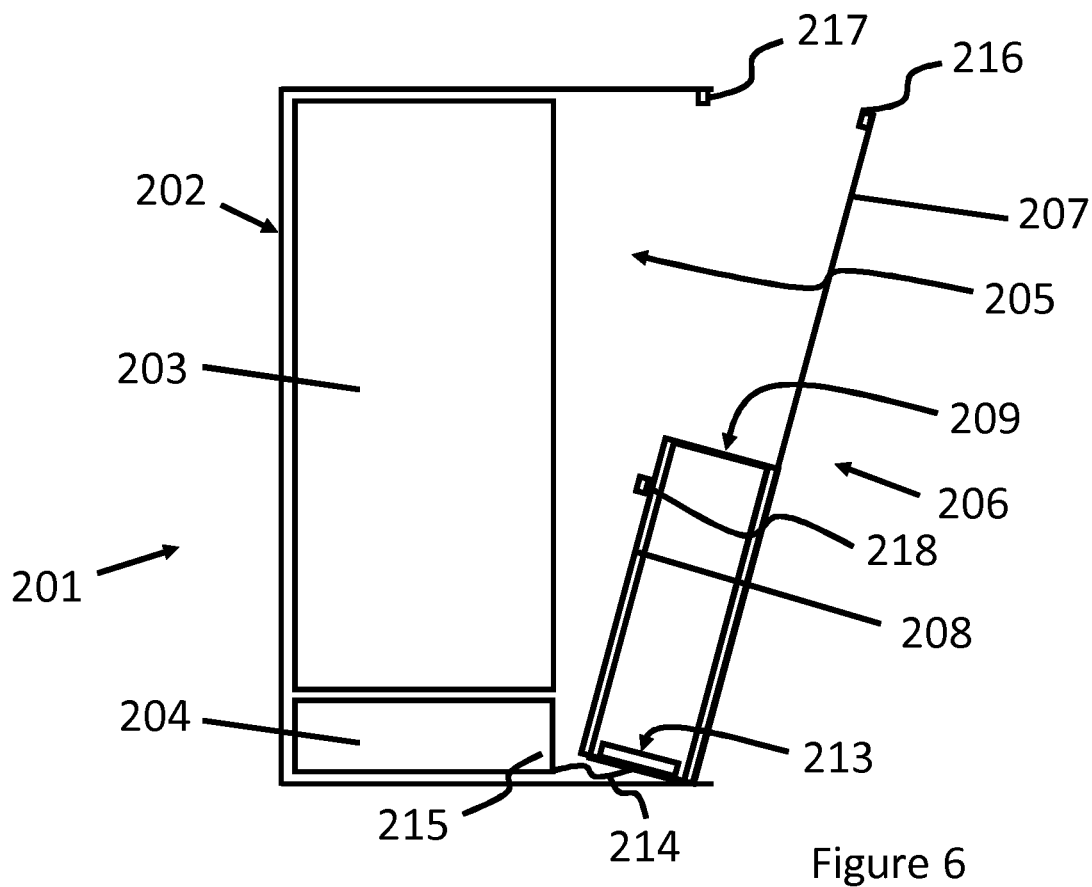
FIG. 6 shows a schematic cross-section of a case according to a first embodiment of the present invention, with the holder in an open position.

FIG. 6 shows a schematic illustration of a case according to a first embodiment of the present invention.

FIG. 6 shows a case 201 according to a first embodiment of the present invention. The case 201 is substantially similar to the case 101 described above with reference to FIGS. 1 to 5. The case 201 comprises a housing 202 and a holder 206. The housing 202 houses a battery 203, circuitry 204 and a cavity 205 for receiving the holder 206. The holder 206 includes an external wall 207 and a tubular internal wall 208 defining a passage 209 having a closed end at a first end of the holder 206 and an open end at a second end of the holder 206. The holder 206 is pivotally coupled to the housing 202 at the first end, such that the holder 206 may be rotated between an open position, where the external wall 207 at the second end of the holder 206 is spaced from the housing 202, and a closed position, where the external wall 207 covers the opening of the cavity 205 and the external wall 207 is in contact with the housing 202 at the second end.

The internal wall 208 is generally circularly cylindrical and comprises a generally circularly cylindrical inner passage 209. The internal wall 208 extends generally along the external wall 207 from the first end in a direction towards the second end. The internal wall 208 extends about 45% of the length of the external wall 207, such that a gap is provided between the internal wall 208 and the external wall 207 at the second end of the holder 206. The internal wall 208 is received in the cavity 205 of the housing 202 when the holder 206 is in the closed position. The external wall 207 is arranged to cover the opening of the cavity 205 to enclose an aerosol-generating device received in the holder 206 within the housing 205 and the external wall 207 of the holder 206 when the holder 206 is in the closed position. The external wall 207 generally forms a side wall of the housing 202 when the holder 206 is in the closed position.

An electrical connector part 213 is arranged at the closed end of the passage 209. The electrical connector part 213 is configured to electrically engage with a complimentary electrical connector part arranged at a distal end of an aerosol-generating device, when the aerosol-generating device is received in the holder 206. The holder 206 further comprises a flexible circuit 214 that is configured to maintain an electrical connection between the circuitry 204 and the electrical connector part 213 regardless of the position of the holder 206 relative to the housing 202.

The case 201 is further provided with magnetic retaining means for releasably retaining the holder in the closed position. The magnetic retaining means comprise a first magnetic material 216 arranged at the second end of the holder and a second magnetic material arranged 217 on the housing at a position adjacent to the second end of the holder when the holder is in the closed position. The first magnetic material 216 is a body of ferrous material and the second magnetic material 217 is a permanent magnet. The first magnetic material 216 and the second magnetic material 217 are arranged to magnetically attract such that the holder 206 is urged or biased into the closed position. The magnetic attraction between the first and second magnetic materials 216, 217 requires a user to apply additional force to the holder 206 to pivot the holder 206 from the closed position to the open position.

The case 201 further comprises a holder position detector in accordance with the present invention. In this embodiment, the holder position detector comprises a push-button switch 218 arranged on the internal wall 208 of the holder 206, adjacent to the open end of the inner passage 209. The push-button switch 218 is arranged on an outer surface of the internal wall 208, facing the housing 202, such that when the holder 206 is in the closed position the push-button switch 218 is pressed between the inner wall 208 of the holder 206 and the housing 202 or one or more of the components housed within the housing 202, such as the battery 203 and the circuitry 204. Accordingly, the push-button switch 218 is depressed or actuated by movement of the holder 206 from the open position to the closed position. Similarly, the push-button switch is released by movement of the holder 206 from the closed position to the open position. As a result, the status of the push-button switch 218 provides an indication of the position of the holder 206 relative to the housing 202.

The push-button switch 218 is electrically connected to the circuitry 204 by a wired connection (not shown). The circuitry 204 is configured to monitor the status of the switch 218 (depressed or released) and thereby monitor the position of the holder. When the circuitry 204 detects that the push-button switch 218 is released, the circuitry 204 is configured to determine that the holder 206 is in the open position, and when the circuitry 204 detects that the push-button stich 218 is depressed, the circuitry 204 is configured to determine that the holder 206 is in the closed position.

Figure 7:
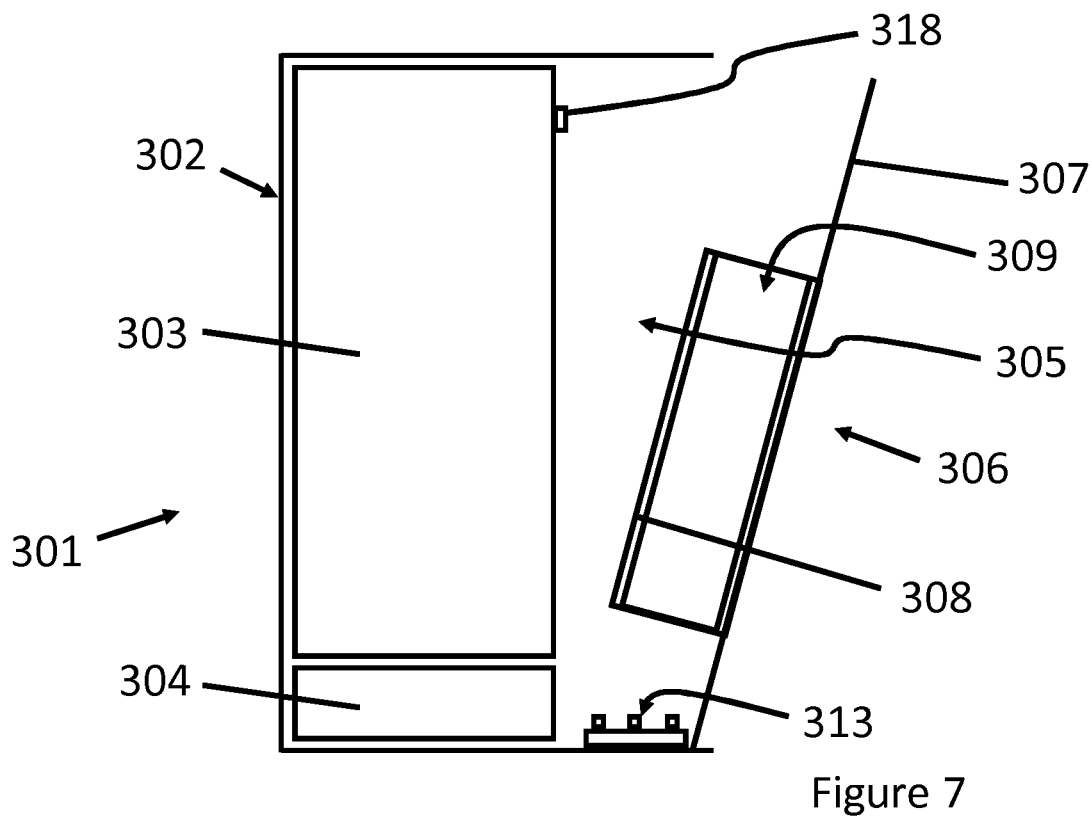
FIG. 7 shows a schematic cross-section of a case according to a second embodiment of the present invention, with the holder in an open position.

FIG. 7 shows a schematic illustration of a case 301 according to a second embodiment of the present invention. The case 301 is substantially similar to the cases 101, 201 described above with reference to FIGS. 1 to 6. The case 301 comprises a housing 302 and a holder 306. The housing 302 houses a battery 303, circuitry 304 and a cavity 305 for receiving the holder 306. The holder 306 includes an external wall 307 and a tubular internal wall 308 defining a passage 309 having open ends at both the first and second ends of the holder 306. The holder 306 is pivotally coupled to the housing 302 at the first end, such that the holder 306 may be rotated between an open position, where the external wall 307 at the second end of the holder 306 is spaced from the housing 302, and a closed position, where the external wall 307 covers the opening of the cavity 305 and the external wall 307 is in contact with the housing 302 at the second end.

The internal wall 308 is generally circularly cylindrical and comprises a generally circularly cylindrical inner passage 309. The internal wall 308 extends generally along the external wall 307 from close to the first end to towards the second end. The internal wall 308 extends about 60% of the length of the external wall 307, such that a gap is provided between the internal wall 308 and the external wall 307 at the first and second ends of the holder. The internal wall 308 is received in the cavity 305 of the housing 302 when the holder 306 is in the closed position. The external wall 307 is arranged to cover the opening of the cavity 305 to enclose an aerosol-generating device received in the holder 306 within the housing 305 and the external wall 307 of the holder 306 when the holder 306 is in the closed position. The external wall 307 generally forms a side wall of the housing 302 when the holder 306 is in the closed position.

The open end of the passage 309 at the first end of the holder 306 enables an aerosol-generating device received in the holder to extend through the passage 309 and contact the housing 302 at a position close to the pivotal coupling.

The case 301 comprises an electrical connector part 313 of in the cavity 305 of the housing 302, close to the pivotal coupling between the housing 302 and the holder 306. The electrical connector part 313 is arranged such that the distal end of an aerosol-generating device received in the holder 306 may contact the electrical connector part 313 when the holder 306 is in the closed position. A complimentary electrical connector part may be arranged at a distal end face of an aerosol-generating device and the second electrical connector part may electrically engage with the electrical connector part 313 when the aerosol-generating device is received in the passage 309 of holder 306 and the holder 306 is in the closed position. In this embodiment, the first electrical connector part 313 is fixedly electrically engaged to the electrical circuitry 304. The electrical connector part at the distal end of the aerosol-generating device is electrically disconnected from the first electrical connector part 313 by pivoting the holder from the closed position to the open position, which moves the distal end face of the aerosol-generating device relative to the housing 302 and the electrical connector part 313.

The case 301 further comprises a holder position detector in accordance with the present invention. In this embodiment, the holder position detector comprises an optical proximity sensor 318 arranged on the housing 302, in the cavity 305, adjacent to the second end of the holder 306. The optical proximity sensor 318 is configured to detect the presence of nearby objects.

In this embodiment, the optical proximity sensor 318 is configured to detect when the aerosol-generating device is received in the holder 306 and the holder 306 is in the closed position. In other words, the optical proximity sensor is configured such that only objects in very close proximity, directly adjacent to the sensor, are detected by the sensor 318. By arranging the sensor 318 adjacent or around the second end of the holder 306, the sensor 318 is exposed to the portion of the holder 306 which does not comprise the internal wall 308. When the aerosol-generating device is not received in the holder 306 and the holder 306 is in the closed position, the optical proximity sensor 318 does not detect the presence of a nearby object. When the aerosol-generating device is received in the holder 306 and the holder 306 is in the closed position, the optical proximity sensor 318 does detect the presence of a nearby object. As a result, the optical proximity sensor 318 only detects the presence of a nearby object when the device is received in the holder 306 and the holder 306 is in the closed position.

The optical proximity sensor 318 is connected to the circuitry 304 by a wired connection (not shown) and the circuitry 304 is configured to monitor the optical proximity sensor 318 to determine when the aerosol-generating device 120 is received in the holder 306 and the holder 306 is in the closed position.

Figure 8:
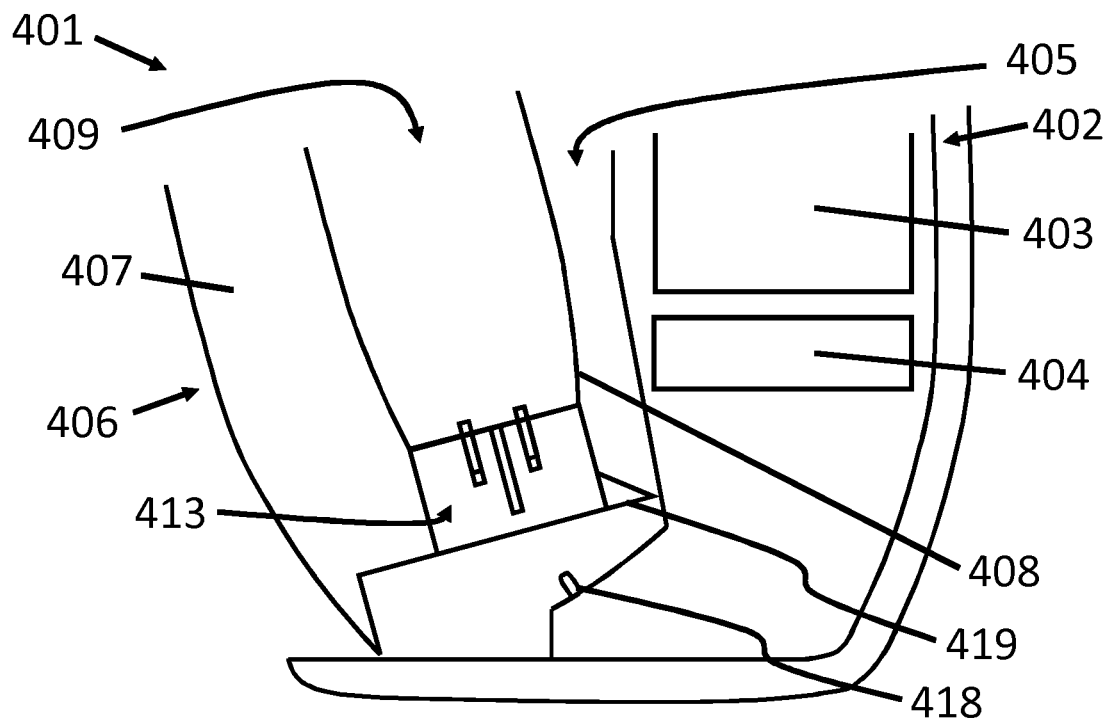
FIG. 8 shows a schematic illustration of a distal portion of a case according to a third embodiment of the present invention, with the holder in an open position.
Figure 9:
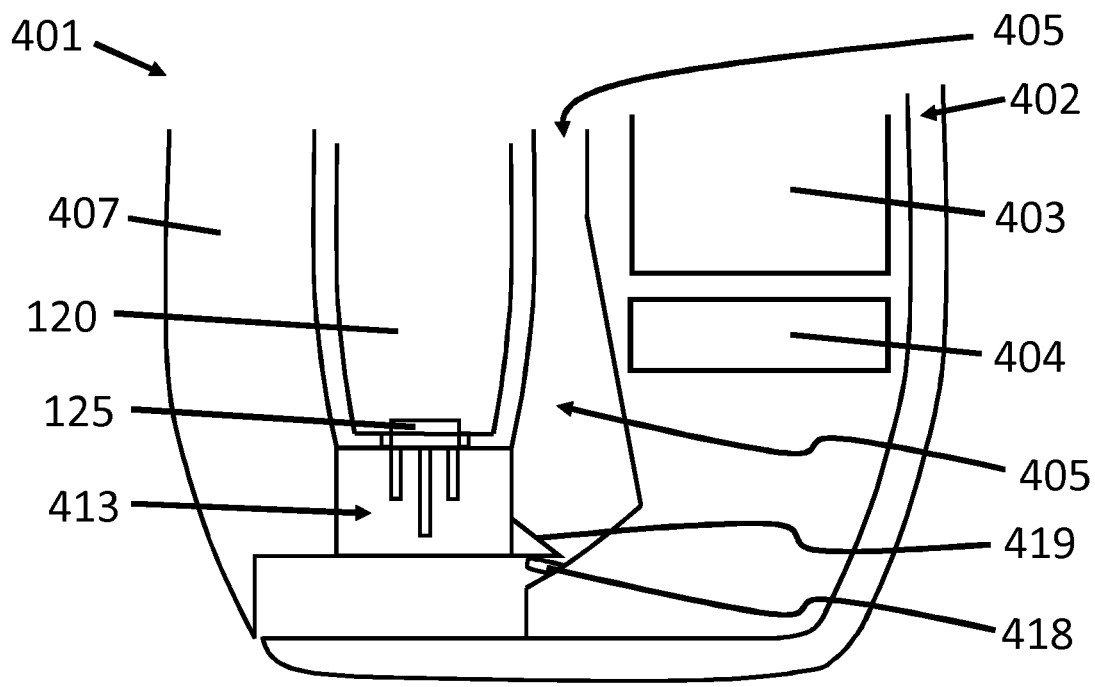
FIG. 9 shows a schematic illustration of a distal portion of the case of FIG. 8, with the aerosol-generating device received in the holder and the holder in a closed position.

FIGS. 8 and 9 show schematic illustrations of a distal portion of a case 401 according to a third embodiment of the present invention. The case 401 is substantially similar to the case 101, 201 and 301 described above with reference to FIGS. 1 to 7. The case 401 comprises a housing 402 and a holder 406. The housing 402 houses a battery 403, circuitry 404 and a cavity 405 for receiving the holder 406. The holder 406 includes an external wall 407 and a tubular internal wall 408 defining a passage 409 having a closed end at a first end of the holder 406 and an open end at a second end of the holder 406. The holder 406 is pivotally coupled to the housing 402 at around the first end, such that the holder 406 may be rotated between an open position, where the external wall 407 at the second end of the holder 406 is spaced from the housing 402, and a closed position, where the external wall 407 covers the opening of the cavity 405 and the external wall 407 is in contact with the housing 402 at the second end.

The internal wall 408 is generally circularly cylindrical and comprises a generally circularly cylindrical inner passage 409. The internal wall 408 extends generally along the external wall 407 from the first end in a direction towards the second end. The internal wall 408 extends about 45% of the length of the external wall 407, such that a gap is provided between the internal wall 408 and the external wall 407 at the second end of the holder 406. The internal wall 408 is received in the cavity 405 of the housing 402 when the holder 406 is in the closed position. The external wall 407 is arranged to cover the opening of the cavity 405 to enclose an aerosol-generating device received in the holder 406 within the housing 405 and the external wall 407 of the holder 406 when the holder 406 is in the closed position. The external wall 407 generally forms a side wall of the housing 402 when the holder 406 is in the closed position.

An electrical connector part 413 is arranged at the closed end of the passage 409. The electrical connector part 413 is configured to electrically engage with the complimentary electrical connector part 125 arranged at a distal end of the aerosol-generating device 120, when the aerosol-generating device 120 is received in the holder 406. The holder 406 further comprises a flexible circuit 414 that is configured to maintain an electrical connection between the circuitry 404 and the electrical connector part 413 regardless of the position of the holder 406 relative to the housing 402. FIG. 9 shows the aerosol-generating device 120 received in the holder 406, with the electrical connector 125 at the distal end of the device 120 in electrical contact with the electrical connector 413 of the case 401 at the second end of the holder 406.

The housing 402 comprises a device holder position detector in the form of a toggle switch 418.

The holder 406 comprises a switch engaging portion in the form of a wedge shaped protrusion 419, which extends into the cavity 405 at the second end of the holder 406. The switch engaging portion 419 of the holder 406 is arranged to contact and actuate the switch 418 on movement of the holder 406 from the open position to the closed position.

The toggle switch 418 is biased to the open position, such that when the holder 406 is not depressing the toggle to the closed position, the toggle returns to the open position.

The circuitry 404 is configured to interrogate the electrical connector part 413 to determine when an aerosol-generating device is connected to the electrical connector part 413. The circuitry 404 is also configured to monitor the position of the toggle switch 418 and determine whether the toggle switch 418 is in the open or the closed position. When the toggle switch 418 is determined to be in the open position, this indicates that the holder 406 is in the open position. When the toggle switch 418 is determined to be in the closed position, this indicates that the holder 406 is in the closed position.

The circuitry 404 is further configured to increment a counter each time it is determined that an aerosol-generating device is received in the holder 406 and the holder 406 is in the closed position. The counter indicates the number of times that the aerosol-generating device 120 has been used.

The circuitry 404 is configured to compare the counter to a first threshold value that is stored in a memory of the circuitry 404. In this embodiment, the first threshold value is 15. The circuitry 404 is configured to trigger a cleaning cycle in the aerosol-generating device 120 when it is determined that the counter is equal to the first threshold value. To trigger the cleaning cycle in the aerosol-generating device 120, the circuitry 404 is configured to send a cleaning signal to the aerosol-generating device 120 via the electrical connector 413. The circuitry 404 is also configured to reset the counter to zero when a cleaning signal is sent to the aerosol-generating device 120 and a cleaning cycle is triggered.

In this embodiment, the circuitry 404 is configured to trigger a cleaning cycle in the aerosol-generating device 120 by sending a cleaning signal to the aerosol-generating device after a charging cycle of the aerosol-generating device has been completed.

When it is determined that the aerosol-generating device 120 is received in the holder 406 and the holder 406 is in the closed position, the circuitry 404 is configured to begin a charging cycle. A charging cycle comprises supplying power to the aerosol-generating device 120 from the battery 403 of the case 400 to recharge the battery 123 of the aerosol-generating device 120. The circuitry 404 is configured to continue to supply power to the battery 123 of the aerosol-generating device until the battery 123 of the aerosol-generating device is fully charged. The circuitry 404 is configured to monitor the charge level of the battery 123 of the aerosol-generating device 120 by monitoring the current and voltage supplied to the electrical connector 413 in a known manner. When the battery 123 of the aerosol-generating device is determined to be fully charged, the charging cycle ends and the cleaning cycle may begin. At the end of the charging cycle, the circuitry 404 supplies a cleaning signal to the aerosol-generating device 120 to begin a cleaning cycle, provided that the conditions for sending a cleaning signal to the aerosol-generating device are met.

In this embodiment, the circuitry 404 is configured to prevent a cleaning signal from being sent to the aerosol-generating device if the toggle switch 418 is in the open position, regardless of the number of the counter. As a result, if the holder 406 is opened before a charging cycle is completed, or after a charging cycle is completed but before a cleaning cycle has been initiated, a cleaning cycle will not be initiated in the aerosol-generating device until the next time the aerosol-generating device is received in the holder 406, the holder 406 is in the closed position and another charging cycle has completed.

In this embodiment, the circuitry 404 comprises a further electrical connector (not shown) for connecting the battery 403 to an external power source for recharging the battery 403. When the counter is determined to be equal to the first threshold value, the electrical circuitry 404 is also configured to prevent a cleaning signal from being sent to the aerosol-generating device 120 unless an external power supply is connected to the battery 403.

If the counter is not equal to the first threshold value, the circuitry 404 is further configured to compare the counter to a second threshold value, greater than the first threshold value. In this embodiment, the second threshold value is 24. If it is determined that the counter is greater than the first threshold value and either equal to or less than the second threshold value, the circuitry 404 is configured to trigger the cleaning cycle in the aerosol-generating device 120 at the end of the charging cycle, provided that an external power supply is connected to the battery 403 of the case 400 and the holder 406 is in the closed position.

If it is determined that the counter is greater than the second threshold value, the circuitry 404 is configured to send a disabling signal to the aerosol-generating device 120. In this embodiment, the circuitry 404 is configured to send the disabling signal to the aerosol-generating device 120 before the charging cycle is initiated. When the circuitry 124 of the aerosol-generating device 120 receives a disabling signal from the circuitry 404, the circuitry 124 of the aerosol-generating device 120 is configured to prevent power from being supplied to the heater 122 until a cleaning cycle has been completed. This should prevent or inhibit use of the aerosol-generating device 120 for an excessive number of times without the heater 122 being cleaned. After the disabling signal has been issued and the following charging cycle has completed, the circuitry 404 is configured to send a cleaning signal to the aerosol-generating device 120 to initiate a cleaning cycle. When the counter is greater than the second threshold value, the control circuitry 404 is configured to send the cleaning signal to the aerosol-generating device 120 provided that the charge level of the battery 404 of the case 400 is greater than a predetermined minimum level and the holder 406 is in the closed position, regardless of whether an external power supply is connected to the battery 403. When the cleaning signal is sent, the control circuitry 404 resets the counter to zero.

When the circuitry 124 of the aerosol-generating device 120 receives a cleaning signal from the circuitry 404, via the electrical connectors 413, 125, the circuitry 123 of the aerosol-generating device 123 initiates a cleaning cycle. In this embodiment, a cleaning cycle comprises supplying power from the battery 123 of the device 120 to the heater 122 to raise the temperature of the heater to a cleaning temperature for a predetermined amount of time. The cleaning temperature is above the normal operating temperature of the heater 122 and is chosen to be a temperature at which aerosol-forming substrate residue undergoes thermal degradation, in order to clean the residue from the heater 122. In this embodiment, the cleaning temperature to which the heater 122 is heated is about 550 degrees Celsius and the predetermined amount of time is about 30 seconds.

It will be appreciated that in other embodiments the threshold values may be different and the conditions in which a signal is prevented from being sent to the aerosol-generating device may be different. It will also be appreciated that in other embodiments a cleaning cycle may be triggered at other times, such as before a charging cycle or during a charging cycle. It will further be appreciated that the cleaning temperature and predetermined amount of time for the cleaning cycle may be different.

It will be appreciated that the above described embodiments are exemplary embodiments of the invention only. It will also be appreciated that features described above in relation to one embodiment of the invention may also be applied to other embodiments of the invention.

The invention claimed is:

1. A case for an aerosol-generating device, the case comprising:
    a housing;
    a holder configured to receive a portion of the aerosol-generating device, the holder being movably couplable to the housing and movable relative to the housing between an open position configured to receive the aerosol-generating device and a closed position configured to store the aerosol-generating device;
    a holder position detector configured to detect whether the holder is in the open position or the closed position, the holder position detector comprising circuitry configured to determine a position of the holder relative to the housing;
    a power supply;
    an electrical connector configured to electrically connect the power supply to an aerosol-generating device received in the holder; and
    power supply control circuitry configured to control a supply of power from the power supply to the aerosol-generating device received in the holder and connected to the electrical connector.

2. The case according to claim 1, wherein the holder position detector circuitry is configured to send a signal to the aerosol-generating device received in the holder and connected to the electrical connector when the holder position detector circuitry determines that the holder is in the closed position and a count of each movement of the holder exceeds a threshold value.

3. The case according to claim 1, wherein the holder position detector further comprises a sensor configured to sense the position of the holder relative to the housing.

4. The case according to claim 3, wherein the sensor is a proximity sensor.

5. The case according to claim 1, wherein the holder position detector further comprises a switch arranged to be actuated on movement of the holder relative to the case between the open position and the closed position.

6. The case according to claim 5, wherein the switch is arranged on or within the housing and the holder comprises a switch engaging portion configured to actuate the switch when the holder is moved between the open position and the closed position.

7. The case according to claim 5, wherein the switch is a toggle switch.

8. The case according to claim 1, wherein the holder position detector circuitry is configured to count each movement of the holder from at least one of the closed position to the open position and the open position to the closed position.

9. The case according to claim 8, wherein the holder position detector circuitry is further configured to compare the count of each movement of the holder to a threshold value.

10. The case according to claim 1, wherein the holder is rotatably coupled to the housing.

11. The case according to claim 10, wherein the holder comprises a first end having an opening configured to receive an aerosol-generating device into the holder and a second end, opposite the first end, the holder being rotatably coupled to the housing at around the second end.

12. An aerosol-generating system comprising an aerosol-generating device and a case for the aerosol-generating device, wherein:
    the aerosol-generating device comprises:
        a cavity configured to receive the aerosol-forming substrate;
        a heater configured to heat an aerosol-forming substrate received in the cavity;
        a power supply; and
        control circuitry configured to control a supply of power between the power supply and the heater; and
    the case is a case according to claim 1.

13. The aerosol-generating system according to claim 12, wherein:
    the case comprises:
        a power supply,
        an electrical connector configured to electrically connect the power supply to an aerosol-generating device received in the holder, and
        power supply control circuitry configured to control the supply of power from the power supply to the aerosol-generating device received in the holder and connected to the electrical connector,
    the holder position detector comprises holder position detector circuitry configured to count each movement of the holder from at least one of the closed position to the open position and the open position to the closed position, and to compare the count of each movement of the holder to a threshold value, and
    the holder position detector circuitry of the case is configured to supply a signal to the aerosol-generating device when the aerosol-generating device is received in the holder and connected to the electrical connector, and when the holder position detector circuitry determines that the holder is in the closed position and the count of each movement of the holder exceeds the threshold value.

14. The aerosol-generating system according to claim 13, wherein the control circuitry of the aerosol-generating device is further configured to supply power to the heater in a cleaning cycle when the control circuitry of the aerosol-generating device receives a signal from the holder position detector circuitry of the case.

* * * * *